United States Patent [19]

Thomissen

[11] Patent Number: 4,484,005

[45] Date of Patent: Nov. 20, 1984

[54] PROCESS FOR THE PREPARATION OF CYCLOHEXYL CYCLOHEXANONE

[75] Inventor: Petrus J. H. Thomissen, Maastricht, Netherlands

[73] Assignee: Stamicarbon B.V., Geleen, Netherlands

[21] Appl. No.: 466,299

[22] Filed: Feb. 14, 1983

[30] Foreign Application Priority Data

Feb. 15, 1982 [NL] Netherlands .................. 8200563

[51] Int. Cl.³ .................... C07C 45/62; C07C 49/303
[52] U.S. Cl. .................................................. 568/350
[58] Field of Search ........................................ 568/350

[56] References Cited

U.S. PATENT DOCUMENTS 2,069,861  2/1937  Phau ................................... 568/350

FOREIGN PATENT DOCUMENTS 397883  9/1933  United Kingdom ............... 568/350

Primary Examiner—Werren B. Lone
Attorney, Agent, or Firm—Cushman, Darby & Cushman

[57] ABSTRACT

Disclosed is a process for the preparation of cyclohexyl cyclohexanone (CHA). Cyclohexanone is self-condensed to yield a mixture of cyclohexylidene cyclohexanone (CHDA), water, and unconverted cyclohexanone. The CHDA in the mixture is directly hydrogenated to CHA under an atmosphere of hydrogen and in the presence of a suitable catalyst, the presence of water and cyclohexanone not affecting the reaction. The CHA may be separated from the other components by, for example, fractional distillation following the hydrogenation.

6 Claims, No Drawings

PROCESS FOR THE PREPARATION OF CYCLOHEXYL CYCLOHEXANONE

BACKGROUND OF THE INVENTION

This invention relates to a process for the preparation of cyclohexyl cyclohexanone (hereinafter referred to as CHA) by hydrogenation in the liquid phase of cyclohexylidene cyclohexanone (hereinafter referred to as CHDA), which is here also understood to mean the tautomer 2-(1-cyclohexenyl)cyclohexanone, which hydrogenation is known from Japanese patent specification No. 47-16434.

The CHDA to be hydrogenated in this process can be obtained by the self-condensation of cyclohexanone according to various known methods, for instance by passing cyclohexanone through an acid ion-exchanger at 90° C. and subjecting the resulting reaction mixture to distillation at reduced pressure (see German patent specification No. 857,960). Similar methods for the implementation of this self-condensation are known from Japanese patent specification No. 70-41377, French patent specification No. 2,186,456 and British patent specification No. 1,493,231.

The reaction mixture obtained in this self-condensation of cyclohexanone contains unconverted cyclohexanone. The fractional distillation further removes the water formed as a result of the self-condensation, such that the CHDA is separated off in virtually pure form.

SUMMARY OF THE INVENTION

It has now been found that the hydrogenation of CHDA to CHA need not be limited to starting with CHDA in virtually pure form, but that it may just as easily be started from the CHDA-containing mixture that is obtained in the self-condensation of cyclohexanone. Water and cyclohexanone per se are still present in the mixture, but preliminary upgrading or purification prior to the hydrogenation is not necessary. It is unobvious that this hydrogenation can be carried out without substantial hydrogenation of the cyclohexanone to cyclohexanol. The water present in the starting mixture does not unfavourably affect the reaction velocity.

DETAILED DISCUSSION

The process according to the present invention is characterized in that the hydrogenation starts from a CHDA-containing mixture obtained from the self-condensation of cyclohexanone, which mixture also contains water and cyclohexanone, and wherein CHA and cyclohexanone are both recovered from the hydrogenation mixture obtained.

The hydrogenation which can be effected at various temperatures within a range of about 10° to about 350° C., can be conducted using hydrogenation catalysts which are per se known. Advantageously, a temperature of from about 50° to about 165° C. is employed so that the hydrogenation may be carried out at atmospheric pressure and in the liquid phase. Very suitable as hydrogenation catalysts are the noble metals of Group VIII of the periodic table, particularly platinum and palladium, or a compound thereof such as an oxide. The catalyst may be employed on a carrier such as carbon, $SiO_2$, MgO an $Al_2O_3$.

By adding to the reaction an alcohol in an amount of from about 2 to about 100 gm per 100 gm of the starting mixture, the hydrogenation rate can be increased substantially. Suitable alcohols are, for instance, methanol, ethanol, propanol, isopropanol, butanol, hexanol and cyclohexanol. The alcohol used need not be water-free. Even using aqueous alcohol such as ethanol which contains 50% water, the hydrogenation rate can still be increased substantially. The amount of alcohol is advantageously chosen such that from about 10 to about 50 gm of alcohol is present per 100 gm of the mixture to be hydrogenated. Below 10 gm of alcohol the increase in the hydrogenation rate is slight while, above 50 gm, the hydrogenation rate hardly increases further.

The partial pressure chosen for the hydrogenation may vary, from about 0.5 to about 50 bar. Advantageously, a partial hydrogen pressure of from 0.5 to 1 bar is selected as a pressure in this range obviates the need to work in pressure equipment.

The mixture which results from the hydrogenation may be upgraded in various ways, for instance by fractional distillation. The desired product, CHA, is accordingly obtained separately from any alcohol that may have been employed, any unconverted CHDA and any cyclohexanone. The alcohol, the CHDA and the cyclohexanone may be reused. The CHA obtained can be used, for instance, in the fragrances industry.

The process according to the present invention will be further described and detailed by means of the following examples.

EXAMPLE I

Cyclohexanone is passed through a column (diameter 20 mm, height 180 mm) filled with 35 gm of strongly acid ion-exchanger (Lewatit SPC 118 W), the space velocity being 8 ml cyclohexanone per ml of ion-exchanger (bulk volume) per hour. By means of a heating jacket placed around the column, the temperature therein is maintained at 90° C. A reaction product is obtained containing 88.6 wt. % cyclohexanone, 9.2 wt. % CHDA, 0.2 wt. % CHA and 2 wt. % water.

Using a 1-liter flask provided with a reflux cooler and an inlet tube for hydrogen, 600 gm of said reaction product is hydrogenated with hydrogen (purity 99%) while stirring in the presence of 245 gm n-hexanol at a temperature of 75° C. and in the presence of a palladium-on-$Al_2O_3$ catalyst (10 wt. % Pd, commercially available under the name Englehard A 720085). An amount of catalyst equivalent to 0.25 gm of palladium per 100 gm CHDA is employed. The hydrogen is introduced at a rate of 0.7 standard liter per minute. After 1 hour, 83% of the CHDA is found, according to gas-chromatographic analysis, to be hydrogenated into CHA and the cyclohexanone is found to be not hydrogenated.

EXAMPLE II

As in Example I, 600 gm of the cyclohexanone-CHDA-CHA-water mixture is hydrogenated in the presence of 165 gm n-hexanol and a platinum-on-carbon catalyst (5 wt. % Pt, commercially available under the name Englehard A 723315) under otherwise unchanged conditions. After 1 hour, 91% of the CHDA is found to be converted into CHA.

EXAMPLE III

As in Example I, the ion-exchanger is maintained at 110° C. and the same space velocity is employed to convert cyclohexanone into a reaction product mixture containing 61.4 wt. % cyclohexanone, 31.8 wt. %

CHDA, 0.8 wt. % CHA and 6 wt. % water. This mixture is hydrogenated in the manner described in Example I at a temperature of 70° C. and in the presence of a palladium-on-carbon catalyst (5 wt. % Pd, commercially available under the name Engelhard A 722441).

600 gm of the mixture and 120 gm ethanol (96 wt. %) are introduced into the reaction flask. An amount of catalyst equivalent to 0.25 gm of palladium per 100 gm CHDA is employed. After 40 minutes the CHDA is found to have been converted virtually completely into CHA. The hydrogenation mixture is then separated from the catalyst, and the separated catalyst is again employed for the hydrogenation of another 600 gm batch of the mixture. After this, 50 more batches are hydrogenated in like fashion. The total amount of hydrogenation mixture (36.2 kg) is subjected to fractional distillation at atmospheric pressure. The distillation yields 6.9 kg of an ethanol-water mixture (72.5 wt. % ethanol), 19.1 kg cyclohexanone and 10.2 kg CHA (purity approximately 96%) which is converted into 8.6 kg virtually pure CHA by distillation at reduced pressure (50 mbar).

What is claimed is:

1. A process for preparing cyclohexyl cyclohexanone, consisting essentially in:
    (a) self-condensing cyclohexanone to obtain a starting mixture containing cyclohexylidene cyclohexanone, uncondensed cyclohexanone, and water,
    (b) subjecting the mixture obtained from step (a) to hydrogenation in the liquid phase, under an atmosphere of hydrogen, at a temperature of about 10° to about 350° C., and in the presence of a hydrogenation catalyst containing a noble metal from Group VIII of the periodic table, and
    (c) recovering cyclohexyl cyclohexanone and cyclohexanone from the hydrogenation reaction mixture which results.

2. The process of claim 1 wherein the hydrogenation is conducted at a temperature of from about 50° to about 165° C.

3. The process of claim 1, wherein said hydrogenation catalyst contains at least one metal selected from the group consisting of platinum and palladium.

4. The process of claim 1 wherein said hydrogenation is conducted in the presence of an alcohol.

5. this process of claim 4, wherein said alcohol is present in an amount from about 10 to about 50 gm per 100 gm of said starting mixture.

6. The process of claim 1 wherein the hydrogenation is conducted with a partial hydrogen pressure of from about 0.5 to about 1 bar.

* * * * *